United States Patent
Yu et al.

(10) Patent No.: US 8,263,374 B2
(45) Date of Patent: Sep. 11, 2012

(54) COMPOSITE YEAST SUITABLE FOR HIGH CONCENTRATION ALCOHOL FERMENTATION FROM SUGAR-CONTAINING RAW MATERIALS

(75) Inventors: Xuefeng Yu, Yichang (CN); Zhihong Li, Yichang (CN); Minghua Yu, Yichang (CN); Juan Yao, Yichang (CN); Zhijun Li, Yichang (CN); Daiwu Liu, Yichang (CN)

(73) Assignee: Angel Yeast Co., Ltd., Yichang (CN)

( * ) Notice: Subject to any disclaimer, the term of this patent is extended or adjusted under 35 U.S.C. 154(b) by 453 days.

(21) Appl. No.: 12/668,578

(22) PCT Filed: Jul. 30, 2008

(86) PCT No.: PCT/CN2008/001395
§ 371 (c)(1),
(2), (4) Date: Jan. 11, 2010

(87) PCT Pub. No.: WO2009/024017
PCT Pub. Date: Feb. 26, 2009

(65) Prior Publication Data
US 2010/0184196 A1    Jul. 22, 2010

(30) Foreign Application Priority Data
Aug. 17, 2007  (CN) .......................... 2007 1 0145242

(51) Int. Cl.
*C12P 7/14* (2006.01)
*C12P 7/06* (2006.01)
*C12N 1/00* (2006.01)
*C12N 1/12* (2006.01)
*A01N 63/04* (2006.01)

(52) U.S. Cl. .................. 435/162; 424/195.16; 435/161; 435/173; 435/254.21; 435/255.2; 435/255.21; 435/440

(58) Field of Classification Search ............. 424/195.16; 435/161, 162, 173, 254.21, 255.2, 255.21, 435/440
See application file for complete search history.

(56) References Cited

U.S. PATENT DOCUMENTS
2007/0036820 A1* 2/2007 Cheung .................... 424/195.16
2007/0053931 A1* 3/2007 Cheung .................... 424/195.16
\* cited by examiner

*Primary Examiner* — Herbert J Lilling
(74) *Attorney, Agent, or Firm* — Clark & Elbing LLP

(57) ABSTRACT

The present invention relates to a composite yeast suitable for high concentration alcohol fermentation from sugar-containing raw materials, characterizing in that the composite yeast comprises any kind of dried yeast selected from Brewers yeast *Saccharomyces cerevisiae* Hansen of *Saccharomyces cerevisiae*, grape wine yeast *Saccharomyces uvarum* Beijerinek, and nutritious materials which are necessary for yeast growth, the nutritious materials include: the dried yeast 40-70 parts by weight, a nitrogen source 20-40 parts by weight, a phosphorous source 5-10 parts by weight, an other inorganic salt 2.5-5 parts by weight, a trace vitamin 1-2.5 parts by weight and a bacteriostatic 0.5-1.2 parts by weight. The present invention further relates to a method for preparation of the composite yeast suitable for high concentration alcohol fermentation from sugar-containing raw materials. Using the composite yeast of the present invention to proceed with sugar fermentation can increase fermentation alcoholicity, decrease residual sugar content, and allows the final alcoholicity of standard raw material, such as sucrose to attain to 14.5-15.5% v/v, and the amount of the residual reducing sugar in the fermentation mash is 0-0.1 wt %.

20 Claims, No Drawings

COMPOSITE YEAST SUITABLE FOR HIGH CONCENTRATION ALCOHOL FERMENTATION FROM SUGAR-CONTAINING RAW MATERIALS

CROSS-REFERENCE TO RELATED APPLICATIONS

This application is the U.S. National Stage of International Application Publication No. PCT/CN2008/001395, filed on Jul. 30, 2008, which claims the benefit of Chinese Patent Application No. CN 200710145242.X, filed on Aug. 17, 2007.

TECHNICAL FIELD

The present invention relates to alcohol fermentation, in particularly, the present invention relates to the composite yeast suitable for high concentration alcohol fermentation from sugar-containing raw materials.

BACKGROUND ART

Alcohol fermentation from sugar-containing raw materials occupies a large proportion of brewing wine and alcohol industry, however, due to the inherent characteristics of sugar-containing raw materials such as single nutrition, lower pH buffer capacity and the like, the sugar-containing raw materials fermentation by using common leaven can not implement completely, especially under the condition of high alcohol concentration. As an example by using sucrose, the common leaven only can maintain the alcoholicity of fermentation in the level of 11-13% v/v, if the alcoholicity continues increasing, the residual sugar-containing raw materials content will become higher and the utilization ratio of the raw materials is deteriorated. Therefore, the issues that how to improve the nutrition condition of the mash of alcohol fermentation from sugar-containing raw materials and how to utilize the raw material components completely are needed to resolve urgently.

As to alcohol fermentation from sugar-containing raw materials, the prior art only directly carried out the fermentation by using yeast or supplied the part of nitrogen source. Furthermore, the prior art did not scientifically analyze the nutrition composition of the fermentation liquor of alcohol fermentation from sugar-containing raw materials, and also did not provide the necessary nutrition for yeast growth, accordingly, the fermentation liquor was not able to be fermented completely, such that the residual sugar content of the mash becomes higher and the utilization ratio of the raw materials was deteriorated.

In addition, Chinese Patent Application Publication No. CN1710084A disclosed a clear process for ethanol fermentation production by using the purified juice of the sugar crops, comprising the step of: A. clarified the mixture solution squeezed from the sugar crops by using bentonite-chitosan complex flocculant clarification technology, and then the separated filtered mud can be used as organic fertilizer, the amount of the pollution is decreased from the source; B. concentrated the purified juice into about 23% sugar content, and proceeded the fermentation by using the concentrated the purified juice and adding yeast thereto, such that the ethanol component of the maturing mash is improved more than 12%, and the discharge of the waste liquid is decreased; C. after the fermentation mash is distilled, the waste mash obtained is subjected to a multiple effect distillation concentration and used as animal protein feed, and achieving none of the waste mash are discharged, solving the problem of the waste mash pollution of the ethanol production.

However, this patent application needed to carry out the bentonite-chitosan complex flocculant clarification technology to the squeeze of the sugar crops, furthermore, needed to concentrate the flocculated sugar cane purified juice and allowed the sugar content reach to about 23%, so it needed some auxiliary equipments such as an additional rapid settling vessel, frame filter and the like, thereby the equipment cost of the process for ethanol fermentation production by using the purified juice of the sugar crops was sharply increased, in the examples, the ethanol composition only reached to 12.6%, the residual sugar content was 0.1%, so the cost of the process for ethanol fermentation production from the purified juice of the sugar crops increased.

For the purpose of overcoming the defect of the prior art, on the basis of fully considering the nutrition condition of sugar-containing raw materials fermentation liquor and the cost of the equipment, the present invention provides a composite yeast suitable for high concentration alcohol fermentation from sugar-containing raw materials. The composite yeast is comprised of a dried yeast and a nutrition source, wherein the dried yeast is a leaven, having strong fermentation activity for the sugar material; the nutrition source includes a inorganic salt or a organic salt, a microelement and a bacteriostatic, providing the necessary nutrition for yeast growth and fermentation, and also inhibiting the other bacteria proliferation, and finally implementing the complete and quick fermentation of sugar-containing raw materials, thus the utilization ratio will be improved without an additional pretreatment to the sugar materials, and the equipment cost of the process is decreased, the alcohol fermentation from sugar-containing raw materials can be proceeded by using the original equipments, and then will implement the complete and quick fermentation of sugar materials, and the utilization ratio of the raw materials will be improved.

SUMMARY OF THE INVENTION

To achieve the above objective, one aspect of the present invention provides a composite yeast suitable for high concentration alcohol fermentation from sugar-containing raw materials, the present invention can overcome the defects of the lower final alcoholicity and the higher residual sugar content during the alcohol fermentation, which exist in the present products, and can remarkably improve efficiency of the alcohol fermentation from sugar-containing raw materials, decrease the general production cost and alleviate the pressure of protecting environment.

One aspect of the present invention provides a composite yeast suitable for high concentration alcohol fermentation from sugar-containing raw materials, characterizing in that the composite yeast comprises any kind of dried yeast selected from Brewers yeast *Saccharomyces cerevisiae* Hansen of *Saccharomyces cerevisiae*, grape wine yeast *Saccharomyces uvarum* Beijerinek, and nutritious materials which are necessary for yeast growth, the nutritious materials include: the dried yeast 40-70 parts by weight, a nitrogen source 20-40 parts by weight, a phosphorous source 5-10 parts by weight, an other inorganic salt 2.5-5 parts by weight, a trace vitamin 1-2.5 parts by weight and a bacteriostatic 0.5-1.2 parts by weight.

Preferably, the yeast is a high temperature-resistant and high active dried yeast, preferably the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate and the mixture of two or more than two of thereof; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof; the other inorganic salt is selected from magnesium sulfate, zinc sulfate and the mixture of two or more thereof the trace vitamin is selected from calcium pantothenate, biotin and vitamin B1 and the mixture of two or more than two thereof; the bacteriostatic is selected from penicillin and Nisin and the mixture thereof.

More preferably, the yeast comprising any kind of dried yeast selected from Brewers yeast *Saccharomyces cerevisiae* Hansen of *Saccharomyces cerevisiae* and grape wine yeast *Saccharomyces uvarum* Beijerinek, and the nutritious materials which are necessary for yeast growth, the nutritious material includes: the dried yeast 50-60 parts by weight, the nitrogen source 25-35 parts by weight, the phosphorous source 6-8 parts by weight, the other inorganic salt 3.5-4.5 parts by weight, the trace vitamin 1-2.5 parts by weight and the bacteriostatic 0.5-1.2 parts by weight.

More preferably, the penicillin is 0.8 million units.

Preferably, the sugar-containing raw materials selects from a squeeze or extract of molasses, or sugar cane, beet and sweet sorghum.

Preferably, the amount of inoculation of the composite yeast is 0.03-0.1% by weight of the amount of mash.

Another aspect of the present invention provides a composite yeast suitable for high concentration alcohol fermentation from sugar-containing raw materials, characterizing in that the composite yeast comprises any kind of dried yeast selected from Brewers yeast *Saccharomyces cerevisiae* Hansen of *Saccharomyces cerevisiae* and grape wine yeast *Saccharomyces uvarum* Beijerinek, and nutritious materials which are necessary for yeast growth, the nutritious materials include: the dried yeast 40-70 parts by weight, a nitrogen source 15-35 parts by weight, a phosphorous source 3-7 parts by weight, a yeast gourmet 10-15 parts by weight and a bacteriostatic 0.5-1.2 parts by weight.

Preferably, the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate and the mixture of two or more than two thereof; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof; the yeast gourmet is selected from a yeast extract powder which are produced by Brewers yeast, *Saccharomyces cerevisiae*, baker's yeast using as raw material, the bacteriostatic is selected from penicillin and Nisin and the mixture thereof.

More preferably, the composite yeast comprising the dried yeast 50-60 parts by weight, the nitrogen source 20-30 parts by weight, the phosphorous source 4-6 parts by weight, the yeast gourmet 11-14 parts by weight and the bacteriostatic 0.5-1.2 parts by weight.

More preferably, the penicillin is 0.8 million units.

Preferably, the sugar-containing raw materials selects from a squeeze or extract of molasses, or sugar cane, beet and sweet sorghum.

Preferably, the amount of inoculation of the composite yeast is 0.03-0.1% by weight of the amount of mash.

Still, a further aspect of the present invention provides a method for preparation of the composite yeast suitable for high concentration alcohol fermentation from sugar-containing raw materials, comprising crashing all of the components separately, excluding a dried yeast; mixing the dried yeast and the crashed material of the other components in a certain weight ratio, and mixing the dried yeast and the other components uniformly by the means of mechanical stirring or manually operate mixing; and obtaining the composite yeast.

The composite yeast of the present invention is mainly suitable for the industry production of brewing wine and alcohol production, which use sucrose and other components containing sucrose (including glucose, fruit sugar) as carbon source.

The sugar-containing raw materials in the present invention is selected from a squeeze or extract of molasses, or sugar cane, beet and sweet sorghum.

During the preparation of the composite yeast of the present invention, the ratio of the above mentioned components can be determined by the raw materials which the producer used, i.e. the difference of sugar source, firstly, crashing all of the other components separately, excluding the dried yeast, by the means of mechanical stirring or manually operate mixing, fully mixing the dried yeast and the other components uniformly, and packing the product according to the specification.

The high temperature-resistant and high active dried yeast is a leaven, which converts the sugar into alcohol, and the other nutritious elements are able to supply and complement the nutritious elements in the fermentation mash under the condition of higher sugar concentration, providing sufficient nutrition elements to fermentation mash, such that the yeast can grow quickly and ferment perfectly, to make sure that the sugar in the mash converts into alcohol completely, and then the utilization ration of the raw material is improved.

The composite yeast of the present invention has some advantages, for example, improving fermentation alcoholicity, decreasing residual sugar content, decreasing the general cost of alcohol fermentation, decreasing pressure of protecting environment, improving the utilization ratio of the raw materials, and also the raw materials are very convenient to obtain, the process is simple and easy to be used. Using the composite yeast of the present invention allows the final alcoholicity of the standard raw materials such as sucrose to reach 14.5-15.5% v/v, the residual reducing sugar in the fermentation mash is 0-0.1wt %.

DESCRIPTION OF PREFERRED EMBODIMENTS

Referring to the following embodiment, the detail description of the composite yeast suitable for high concentration alcohol fermentation from sugar-containing raw materials according to the present invention will be made, and it is understood that the detailed description only intends to understand the present invention, can not be considered to limit the scope of the present invention.

In one embodiment of this invention, providing a composite yeast suitable for high concentration alcohol fermentation from sugar-containing raw materials, characterizing in that the composite yeast comprises any kind of dried yeast selected from Brewers yeast *Saccharomyces cerevisiae* Hansen of *Saccharomyces cerevisiae*, grape wine yeast *Saccharomyces uvarum* Beijerinek, and nutritious materials which are necessary for yeast growth, the nutritious materials include: the dried yeast 40-70 parts by weight, a nitrogen source 20-40 parts by weight, a phosphorous source 5-10 parts by weight, an other inorganic salt 2.5-5 parts by weight, a trace vitamin 1-2.5 parts by weight and a bacteriostatic 0.5-1.2 parts by weight.

In a preferred embodiment, the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate and the mixture of two or more than two of thereof; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof; the other inorganic salt is selected from magnesium sulfate, zinc sulfate and the mixture of two or more thereof; the trace vitamin is selected from calcium pantothenate, biotin and vitamin B1 and the mixture of two or more than two thereof; the bacteriostatic is selected from penicillin and Nisin and the mixture thereof.

In a further preferred embodiment, the yeast comprising any kind of dried yeast selected from Brewers yeast *Saccharomyces cerevisiae* Hansen of *Saccharomyces cerevisiae* and grape wine yeast *Saccharomyces uvarum* Beijerinek, and the nutritious materials which are necessary for yeast growth, the nutritious material includes: the dried yeast 50-60 parts by weight, the nitrogen source 25-35 parts by weight, the phosphorous source 6-8 parts by weight, the other inorganic salt 3.5-4.5 parts by weight, the trace vitamin 1-2.5 parts by weight and the bacteriostatic 0.5-1.2 parts by weight.

In a further preferred embodiment, the penicillin is 0.8 million units.

In a preferred embodiment, the sugar-containing raw materials selects from a squeeze or extract of molasses, or sugar cane, beet and sweet sorghum.

In a preferred embodiment, the amount of inoculation of the composite yeast is 0.03-0.1% by weight of the amount of mash.

In another embodiment of the present invention providing a composite yeast suitable for high concentration alcohol fermentation from sugar-containing raw materials, characterizing in that the composite yeast comprises any kind of dried yeast selected from Brewers yeast *Saccharomyces cerevisiae* Hansen of *Saccharomyces cerevisiae* and grape wine yeast *Saccharomyces uvarum* Beijerinek, and nutritious materials which are necessary for yeast growth, the nutritious materials include: the dried yeast 40-70 parts by weight, a nitrogen source 15-35 parts by weight, a phosphorous source 3-7 parts by weight, a yeast gourmet 10-15 parts by weight and a bacteriostatic 0.5-1.2 parts by weight.

In a preferred embodiment, the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate and the mixture of two or more than two thereof; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof; the yeast gourmet is selected from a yeast extract powder which are produced by Brewers yeast, *Saccharomyces cerevisiae*, baker's yeast using as raw material, the bacteriostatic is selected from penicillin and Nisin and the mixture thereof.

In a further preferred embodiment, the composite yeast comprising the dried yeast 50-60 parts by weight, the nitrogen source 20-30 parts by weight, the phosphorous source 4-6 parts by weight, the yeast gourmet 11-14 parts by weight and the bacteriostatic 0.5-1.2 parts by weight.

In a further preferred embodiment, the penicillin is 0.8 million units.

In a preferred embodiment, the sugar-containing raw materials selects from a squeeze or extract of molasses, or sugar cane, beet and sweet sorghum.

In a preferred embodiment, the amount of inoculation of the composite yeast is 0.03-0.1% by weight of the amount of mash.

Still, in a further embodiment of the present invention providing a method for preparation of composite yeast suitable for high concentration alcohol fermentation from sugar-containing raw materials, comprising crashing all of the components separately, excluding dried yeast; mixing the dried yeast and the crashed material of the other components in a certain weight ratio, and mixing the dried yeast and the other components uniformly by the means of mechanical stirring or manually operate mixing; and obtaining the composite yeast.

The composite yeast of the present invention is mainly suitable for the industry production of brewing wine and alcohol production which uses sucrose and the other components containing sucrose (including glucose, fruit sugar) as carbon source.

The sugar-containing raw materials in the present invention is selected from a squeeze or extract of molasses, or sugar cane, beet and sweet sorghum.

During the preparation of the composite yeast of the present invention, the ratio of the above mentioned components can be determined by the raw materials which the producer used, i.e. the difference of sugar source, firstly, crashing all of the other components separately, excluding the dried yeast, by the means of mechanical stirring or manually operate mixing, fully mixing the dried yeast and the other components uniformly, and packing the product according to the specification.

EXAMPLE 1

The Composite Yeast 1 Suitable for High Concentration Alcohol Fermentation from Sugar-Containing Raw Materials and the Preparation Thereof According the component ratio of composite yeast 1, firstly, crashing urea, ammonium dihydrogen phosphate, magnesium sulfate monohydrate and zinc sulfate monohydrate separately, and then mechanically stirring following components: high temperature-resistant high active dried Brewers yeast 57 parts by weight, urea 30 parts by weight, ammonium dihydrogen phosphate 7.5 parts by weight, magnesium sulfate monohydrate 2.5 parts by weight, zinc sulfate monohydrate 1 parts by weight, biotin 0.5 parts by weight, vitamin B1 0.5 parts by weight, calcium pantothenate 0.5 parts by weight and 0.8 million unit penicillin 0.5 parts by weight, then obtaining a composite yeast 1 suitable for high concentration alcohol fermentation from sugar-containing raw materials. Then, packing the resultant yeast into package on basis of the certain weight, and then obtaining the product of composite yeast 1.

EXAMPLE 2

The Composition Yeast 1 Using in High Concentration Alcohol Fermentation from Sucrose The composite yeast 1 produced from Example 1 is used in the sucrose solution with about 25% sucrose content to carry out alcohol fermentation.

The amount of inoculation of the composite yeast 1 in the above sucrose solution is by weight of 0.05% of mash, and adjusting the mash pH to 7.5-8.5 by adding sodium carbonate, fermented for about 70 hours under 32-35° C. Meanwhile, high temperature-resistant and high active dried yeast is directly inoculated in the same amount, which is used as comparison, fermented for about 120 hours. The results obtained as follows:

TABLE 1

| the fermentation result of composite yeast 1 in the sucrose solution | | |
| --- | --- | --- |
| index | comparison | Adding composite yeast 1 |
| Original sugar content (Bx) | 26.2 | 26.2 |
| alcoholicity (% v/v) | 11.7 | 15.2 |
| Residual sugar content (g/l) | 5.68 | 0.06 |
| Fermented time (hr) | 120 | 70 |

It can be seen from the result of table 1: using the high temperature-resistant and high active dried yeast alone to proceed the sugar fermentation, after fermented for 120 hours, the residual sugar content of the mash is 5.68 g/l, and the alcoholicity is 11.7% v/v; however, after fermented for 70 hours, the residual sugar content of the mash is 0.06g/l, and the alcoholicity is 15.2% v/v by using the composite yeast 1 according to Example 1 of the present invention.

EXAMPLE 3

The Composite Yeast 2 Suitable for High Concentration Alcohol Fermentation from Sugar-Containing Raw Materials and the Preparation Thereof According the component ratio of composite yeast 2, firstly, crashing ammonium sulfate, ammonium dihydrogen phosphate and the yeast gourmet separately, then mechanically stirring following components: high temperature-resistant and high active dried yeast 55 parts by weight, ammonium sulfate 25 parts by weight, ammonium dihydrogen phosphate 7.5 parts by weight, yeast gourmet 22 parts by weight and 0.8 million units penicillin 1.0 parts by weight, and then obtaining the composite yeast 2 suitable for high concentration alcohol fermentation from sugar-containing raw materials. Then, packing the resultant yeast into package on basis of the certain weight, and then obtaining the product of composite yeast 2.

EXAMPLE 4

Composition Yeast 2 Used in High Concentration Alcohol Fermentation from Molasses The composite yeast 2 produced from Example 3 is used in the sucrose molasses solution with about 30Brix total sugar content to carry out alcohol fermentation.

The amount of inoculation of the composite yeast 2 in the above sucrose molasses solution is by weight of 0.08% of mash, fermented for about 45 hours under 32-35° C. Meanwhile, a high temperature-resistant and high active dried yeast is directly inoculated in the same amount, which is used as comparison, fermented for about 72 hours. The results obtained as follows:

TABLE 2

| the fermentation result of composition yeast 2 in the sucrose molasses solution | | |
| --- | --- | --- |
| index | comparison | Adding composite yeast 2 |
| Original sugar content (Bx) | 30 | 30 |
| alcoholicity (% v/v) | 8.7 | 12.3 |
| Residual sugar content (g/l) | 8.0 | 4.5 |
| Fermented time (hr) | 72 | 45 |

It can be seen from the result of table 2: using the high temperature-resistant and high active dried yeast alone to proceed the sucrose molasses fermentation, after fermented for 72 hours, the residual sugar content of the mash is 8.0Bx, and the alcoholicity is 8.7% v/v; however, after fermented for 45 hours, residual sugar content of the mash is 4.5Bx, and the alcoholicity is 12.3% v/v by using the composite yeast 2 according to Example 3 of the present invention to proceed molasses fermentation.

EXAMPLE 5

The Composite Yeast 3 Suitable for High Concentration Alcohol Fermentation from Sugar-Containing Raw Materials and the Preparation Thereof According the component ratio of composite yeast 3, firstly, crashing urea, ammonium dihydrogen phosphate, magnesium sulfate monohydrate and zinc sulfate monohydrate separately, and then mechanically stirring following components: high temperature-resistant high active dried Brewers yeast 55 parts by weight, urea 32.5 parts by weight, ammonium dihydrogen phosphate 8 parts by weight, magnesium sulfate monohydrate 2 parts by weight, zinc sulfate monohydrate 0.5 parts by weight, biotin 0.5 parts by weight, vitamin B1 0.5 parts by weight, calcium pantothenate 0.5 parts by weight and 0.8 million unit penicillin 0.5 parts by weight, then obtaining a composite yeast 3 suitable for high concentration alcohol fermentation from sugar-containing raw materials. Then, packing the resultant yeast into package on basis of the certain weight, and then obtaining the product of composite yeast 3.

EXAMPLE 6

The Composition Yeast 3 Using in High Concentration Alcohol Fermentation from Sucrose The composite yeast 3 produced from Example 5 is used in the sucrose solution with about 28% sucrose content to carry out alcohol fermentation.

The amount of inoculation of the composite yeast 3 in the above sucrose solution is by weight of 0.05% of mash, and adjusting the mash pH to 7.5-8.5 by adding sodium carbonate, fermented for about 75 hours under 32-35° C. Meanwhile, high temperature-resistant and high active dried yeast is directly inoculated in the same amount, which is used as comparison, fermented for about 120 hours. The results obtained as follows:

TABLE 3 the fermentation result of composite yeast 3 in the sucrose solution

| index | comparison | Adding composite yeast 3 |
| --- | --- | --- |
| Original sugar content (Bx) | 27.5 | 27.5 |
| alcoholicity (% v/v) | 11.4 | 15.7 |
| Residual sugar content (g/l) | 6.84 | 0.13 |
| Fermented time (hr) | 120 | 75 |

It can be seen from the result of table 3: using the high temperature-resistant and high active dried yeast alone to proceed the sugar fermentation, after fermented for 120 hours, the residual sugar content of the mash is 6.84 g/l, and the alcoholicity is 11.4% v/v; however, after fermented for 75 hours, the residual sugar content of the mash is 0.13g/l, and the alcoholicity is 15.7% v/v by using the composite yeast 3 according to Example 5 of the present invention.

A conclusion can be made that composite yeast of the present invention has some advantages, for example, for example, improving fermentation alcoholicity, decreasing residual sugar content, decreasing the general cost of alcohol fermentation, decreasing pressure of protecting environment, improving the utilization ratio of the raw materials, and also the raw materials are very convenient to obtain, the process is simple and easy to be used. Using the composite yeast of the present invention allows the final alcoholicity of the standard raw materials such as sucrose to reach 14.5-15.7% v/v, the residual reducing sugar in the fermentation mash is 0-0.1wt %.

Those skilled in the art should appreciate that the examples and embodiments described herein above are for illustrative purposes only and not to limit the scope of the present invention, various of modifications, combinations and sub-combinations and changes can be made if necessary, all of the modifications, combinations, sub-combinations, changes and equivalents are fallen in the scope of the following claims.

What we claim:

1. A composite yeast suitable for high concentration alcohol fermentation from sugar-containing raw materials, wherein the composite yeast comprises any kind of dried yeast selected from Brewers yeast *Saccharomyces cerevisiae* Hansen of *Saccharomyces cerevisiae*, grape wine yeast *Saccharomyces uvarum* Beijerinek, and nutritious materials which are necessary for yeast growth, the nutritious materials include: the dried yeast 40-70 parts by weight, a nitrogen source 20-40 parts by weight, a phosphorous source 5-10 parts by weight, an other inorganic salt 2.5-5 parts by weight, a trace vitamin 1-2.5 parts by weight and a bacteriostatic 0.5-1.2 parts by weight.

2. The composite yeast according to claim 1, wherein the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof; the other inorganic salt is selected from magnesium sulfate, zinc sulfate and the mixture of two or more thereof; the trace vitamin is selected from calcium pantothenate, biotin and vitamin B1 and the mixture of two or more than two thereof; the bacteriostatic is selected from penicillin and Nisin and the mixture thereof.

3. The composite yeast according to claim 1, wherein the yeast comprising any kind of dried yeast selected from Brewers yeast *Saccharomyces cerevisiae* Hansen of *Saccharomyces cerevisiae* and grape wine yeast *Saccharomyces uvarum* Beijerinek, and the nutritious materials which are necessary for yeast growth, the nutritious material includes: the dried yeast 50-60 parts by weight, the nitrogen source 25-35 parts by weight, the phosphorous source 6-8 parts by weight, the other inorganic salt 3.5-4.5 parts by weight, the trace vitamin 1-2.5 parts by weight and the bacteriostatic 0.5-1.2 parts by weight.

4. A composite yeast suitable for high concentration alcohol fermentation from sugar-containing raw materials, wherein the composite yeast comprises any kind of dried yeast selected from Brewers yeast *Saccharomyces cerevisiae* Hansen of *Saccharomyces cerevisiae* and grape wine yeast *Saccharomyces uvarum* Beijerinek, and nutritious materials which are necessary for yeast growth, the nutritious materials include: the dried yeast 40-70 parts by weight, a nitrogen source 15-35 parts by weight, a phosphorous source 3-7 parts by weight, a yeast gourmet 10-15 parts by weight and a bacteriostatic 0.5-1.2 parts by weight.

5. The composite yeast according to claim 4, wherein the yeast is any kind of dried yeast selected from Brewers yeast *Saccharomyces cerevisiae* Hansen of *Saccharomyces cerevisiae* and grape wine yeast *Saccharomyces uvarum* Beijerinek, the nitrogen source is selected from ammonium sulfate, urea, and ammonium nitrate and the mixture of two or more than two thereof; the phosphorous source is selected from ammonium dihydrogen phosphate, ammonium phosphate dibasic, potassium dihydrogen phosphate, dipotassium hydrogen phosphate, sodium dihydrogen phosphate, dibasic sodium phosphate and the mixture of two or more than two thereof;
the yeast gourmet is selected from a yeast extract powder which are produced by Brewers yeast, *Saccharomyces cerevisiae*, baker's yeast using as raw material, the bacteriostatic is selected from penicillin and Nisin and the mixture thereof.

6. The composite yeast according to claim 4, comprising the dried yeast 40-70 parts by weight, the nitrogen source 15-35 parts by weight, the phosphorous source 3-7 parts by weight, the yeast gourmet 10-15 parts by weight and the bacteriostatic 0.5-1.2 parts by weight.

7. The composite yeast according to claim 2, wherein the penicillin is 0.8 million units.

8. The composite yeast according to claim 1, wherein the sugar-containing raw materials selects from a squeeze or extract of molasses, or sugar cane, beet and sweet sorghum.

9. The composite yeast according to claim 1, wherein the amount of inoculation of the composite yeast is 0.03-0.1% by weight of the amount of mash.

10. A method for the preparation of the composite yeast suitable for high concentration alcohol fermentation from sugar-containing raw materials, wherein the composite yeast comprises any kind of dried yeast selected from Brewers yeast *Saccharomyces cerevisiae* Hansen of *Saccharomyces cerevisiae*, grape wine yeast *Saccharomyces uvarum* Beijerinek, and nutritious materials which are necessary for yeast growth, the nutritious materials include: the dried yeast 40-70 parts by weight, a nitrogen source 20-40 parts by weight, a phosphorous source 5-10 parts by weight, an other inorganic salt 2.5-5 parts by weight, a trace vitamin 1-2.5 parts by weight and a bacteriostatic 0.5-1.2 parts by weight, comprising crashing all of the components separately, excluding a dried yeast; mixing the dried yeast and the crashed material of the other components in a certain weight ratio, and mixing the dried yeast and the other components uniformly by the means of mechanical stirring or manually operate mixing; and obtaining the composite yeast.

11. The composite yeast according to claim 2, wherein the yeast comprising any kind of dried yeast selected from Brewers yeast *Saccharomyces cerevisiae* Hansen of *Saccharomyces cerevisiae* and grape wine yeast *Saccharomyces uvarum* Beijerinek, and the nutritious materials which are necessary for yeast growth, the nutritious material includes: the dried yeast 50-60 parts by weight, the nitrogen source 25-35 parts by weight, the phosphorous source 6-8 parts by weight, the other inorganic salt 3.5-4.5 parts by weight, the trace vitamin 1-2.5 parts by weight and the bacteriostatic 0.5-1.2 parts by weight.

12. The composite yeast according to claim 5, comprising the dried yeast 40-70 parts by weight, the nitrogen source 15-35 parts by weight, the phosphorous source 3-7 parts by weight, the yeast gourmet 10-15 parts by weight and the bacteriostatic 0.5-1.2 parts by weight.

13. The composite yeast according to claim 5, wherein the penicillin is 0.8 million units.

14. The composite yeast according to claim 2, wherein the sugar-containing raw materials selects from a squeeze or extract of molasses, or sugar cane, beet and sweet sorghum.

15. The composite yeast according to claim 2, wherein the amount of inoculation of the composite yeast is 0.03-0.1% by weight of the amount of mash.

16. The composite yeast according to claim 4, wherein the sugar selects from a squeeze or extract of molasses, or sugar cane, beet and sweet sorghum.

17. The composite yeast according to claim 4, the amount of inoculation of the composite yeast is 0.03-0.1% by weight of the amount of mash.

18. The composite yeast according to claim 5, wherein the sugar-containing raw materials selects from a squeeze or extract of molasses, or sugar cane, beet and sweet sorghum.

19. The composite yeast according to claim 5, wherein the amount of inoculation of the composite yeast is 0.03-0.1% by weight of the amount of mash.

20. A method for the preparation of the composite yeast suitable for high concentration alcohol fermentation from sugar-containing raw materials, wherein the composite yeast comprises any kind of dried yeast selected from Brewers yeast *Saccharomyces cerevisiae* Hansen of *Saccharomyces cerevisiae* and grape wine yeast *Saccharomyces uvarum* Beijerinek, and nutritious materials which are necessary for yeast growth, the nutritious materials include: the dried yeast 40-70 parts by weight, a nitrogen source 15-35 parts by weight, a phosphorous source 3-7 parts by weight, a yeast gourmet 10-15 parts by weight and a bacteriostatic 0.5-1.2 parts by weight, comprising crashing all of the components separately, excluding a dried yeast; mixing the dried yeast and the crashed material of the other components in a certain weight ratio, and mixing the dried yeast and the other components uniformly by the means of mechanical stirring or manually operate mixing; and obtaining the composite yeast.

\* \* \* \* \*